(12) United States Patent
Marchesi

(10) Patent No.: US 11,913,147 B2
(45) Date of Patent: Feb. 27, 2024

(54) TEXTILE SENSOR FOR THE DETECTION OF LIQUIDS AND TEMPERATURE, AND METHOD OF MAKING SAME

(71) Applicant: KNITRONIX S.R.L., Florence (IT)

(72) Inventor: Riccardo Marchesi, Vaglia (IT)

(73) Assignee: KNITRONIX S.R.L., Florence (IT)

( * ) Notice: Subject to any disclaimer, the term of this patent is extended or adjusted under 35 U.S.C. 154(b) by 70 days.

(21) Appl. No.: 17/638,319

(22) PCT Filed: Aug. 26, 2020

(86) PCT No.: PCT/IB2020/057954
§ 371 (c)(1),
(2) Date: Feb. 25, 2022

(87) PCT Pub. No.: WO2021/038454
PCT Pub. Date: Mar. 4, 2021

(65) Prior Publication Data
US 2022/0307166 A1    Sep. 29, 2022

(30) Foreign Application Priority Data
Aug. 26, 2019   (IT) .................. 102019000015051

(51) Int. Cl.
*D04B 1/12* (2006.01)
*A61F 5/48* (2006.01)

(52) U.S. Cl.
CPC ................. *D04B 1/12* (2013.01); *A61F 5/48* (2013.01); *D10B 2401/02* (2013.01); *D10B 2403/02431* (2013.01)

(58) Field of Classification Search
CPC ... D04B 1/12; D04B 1/14; D04B 7/30; D04B 11/26; D10B 2403/02431
See application file for complete search history.

(56) References Cited

U.S. PATENT DOCUMENTS 10,761,605 B1 * 9/2020 Sunshine ........... A41D 19/0024
10,945,663 B2 * 3/2021 Bozkurt ............... G01N 27/048
(Continued)

FOREIGN PATENT DOCUMENTS

DE   10 2010 060222 A1    5/2012
DE   10 2018 210036 A1   12/2019
(Continued)

*Primary Examiner* — Danny Worrell
(74) *Attorney, Agent, or Firm* — Maschoff Brennan

(57) ABSTRACT

A textile device for detecting liquids comprising a matrix fabric obtained by knitting, a first non-insulated conductive wire and a second non-insulated conductive wire knitted with the matrix fabric, a source of electric energy connected to the non-insulated conductive wires in order to create a first electric circuit and to have a potential difference between the non-insulated conductive wires, an electrical resistance measuring device configured to measure the electric resistance R in the first electric circuit. The textile device is configured in such a way that, when the non-insulated conductive wires electrically connect by means of a liquid, the electrical resistance measuring system measures a variation of electric resistance R in said first electric circuit. Furthermore, at least one insulated conductive wire is provided connected to a source of electric energy in order to create a second electric circuit.

6 Claims, 3 Drawing Sheets

(56) References Cited

U.S. PATENT DOCUMENTS

| | | | |
|---|---|---|---|
| 2009/0013728 A1* | 1/2009 | Dias | D04B 1/14 66/171 |
| 2015/0305676 A1* | 10/2015 | Shoshani | A61B 5/6805 66/202 |
| 2016/0186366 A1* | 6/2016 | Mcmaster | D04B 1/24 28/143 |
| 2018/0279930 A1* | 10/2018 | Coppedè | C12Q 1/002 |
| 2020/0207057 A1* | 7/2020 | Bowles | B32B 5/26 |
| 2021/0172096 A1* | 6/2021 | Kondo | D03D 15/497 |
| 2022/0003613 A1* | 1/2022 | Chahine | G01K 7/16 |
| 2022/0007986 A1* | 1/2022 | Chahine | A61B 5/304 |
| 2023/0151514 A1* | 5/2023 | Isaia | A61B 5/6804 66/202 |

FOREIGN PATENT DOCUMENTS

| | | |
|---|---|---|
| WO | 2008115987 A2 | 9/2008 |
| WO | 2009/001108 A1 | 12/2008 |

* cited by examiner

TEXTILE SENSOR FOR THE DETECTION OF LIQUIDS AND TEMPERATURE, AND METHOD OF MAKING SAME

FIELD OF THE INVENTION

The present invention relates to the field of environmental sensors.

In particular, the invention relates to a textile sensor for detecting liquids and/or humidity.

DESCRIPTION OF THE PRIOR ART

As well known, a recurring problem in health facilities that carry out long-term hospitalization is that of the formation of bedsores. The formation of pressure sores is mainly caused by poor blood circulation in the contact areas between the body and the mattress on which the patient lies, but it is considerably accelerated if the contact area is wet. Patients lying on moist tissue are in fact much more likely to develop pressure sores in a very short time. This picture is made more complex if the patient is an elderly person with incontinence.

Furthermore, although the procedures indicate that between one patient and another there must be a perfect sterilization of the layers of tissue that are in contact with the body, the loss of physiological fluids that are not promptly removed by the paramedics greatly increases the risk of formation of colonies of bacteria that proliferate on the outermost layers of the mattress and the formation of sores.

There are systems with humidity sensors placed between the patient's body and the top layer of the mattress. These systems allow immediate intervention by healthcare professionals in the event of fluid leaks. Furthermore, if the signal coming from the sensor is brought into the control room of the ward, it can allow considerable savings in personnel, since it will no longer be necessary to perform a complete control of all patients at each shift, but it will be sufficient to assist only those patients whose beds they are damp. A system that alerts personnel of any loss therefore allows costs to be contained and a more efficient service to be guaranteed.

For example, WO2008115987 describes a device for detecting humidity on a mattress cover, in which there are conductive circuits arranged over the entire surface so as to ensure equal sensitivity to humidity in any position of the mattress cover. Moisture is detected by applying a different voltage level to adjacent conductive circuits and measuring the current flowing between them. In particular, the conductive circuits are inserted into a support layer or affixed to it by moulding. The support layer, preferably waterproof, constitutes the mattress cover.

This system, however, has the main drawback of being not very suitable for being subjected to deformation, since the conductive circuits, whether inserted or printed, necessarily have different elastic properties with respect to the support layer.

In fact, in the event that the circuits are more rigid than the support, for example in the case of textile support, they risk being damaged during flexion or extension of the mattress cover, very frequent actions during patient handling or folding of the mattress cover. If, on the other hand, the support was rigid or semi-rigid, the circuits would be protected from damage, but the mattress cover would result in less patient comfort and would be difficult to fold when not in use.

Furthermore, the device described in WO2008115987, due to its conformation, cannot be used, for example, for the detection of liquids inside buildings or other contexts where it is necessary to detect a leak.

There is therefore a need for a device for detecting liquids that can solve the aforementioned problems.

SUMMARY OF THE INVENTION

It is therefore a feature of the present invention to provide a textile device for detecting liquids that has the same resistance against deformation, flexion and extension of a traditional tissue.

It is also a feature of the present invention to provide such a device that is able to detect changes in humidity in the air or in a material adjacent to the device.

It is still a feature of the present invention to provide such a device that is able to detect leaks of liquids inside buildings.

It is a further feature of the invention to provide such a device that allows to detect temperature variations.

It is also a feature of the present invention to provide a method for creating said device, according to variable shapes and sizes.

These and other objects are achieved by a textile device for detecting liquids according to claims from 1 to 8.

The knitting of the non-insulated conductive wires with the matrix fabric gives to the textile device higher extensibility and flexibility with respect to the prior art.

Furthermore, the creation by knitting allows to provide the textile device with complex geometries and lengths that are much higher than the prior art.

In addition to detecting leaks in hospital beds, there are numerous possible applications of the present invention.

For example, an application concerns the monitoring of rainwater leaks in the roofs of historic buildings. A strip of the textile device, according to the present invention, can be spread in the attic of a building, arranging it in parallel strips all electrically connected to the same electrical resistance measuring device, so as to completely cover the floor surface. In this way, any dripping water coming from the roof would be immediately detected, allowing prompt intervention.

Another possible application concerns the monitoring of the temperature and conductivity of a user's skin or GSR (Galvanic Skin Response).

According to a further aspect of the present invention, a method for creating the textile device is claimed, according to the present invention.

BRIEF DESCRIPTION OF THE DRAWINGS

Further characteristic and/or advantages of the present invention are more bright with the following description of an exemplary embodiment thereof, exemplifying but not limitative, with reference to the attached drawings in which.

DESCRIPTION OF A PREFERRED EXEMPLARY EMBODIMENT

Figure 1:
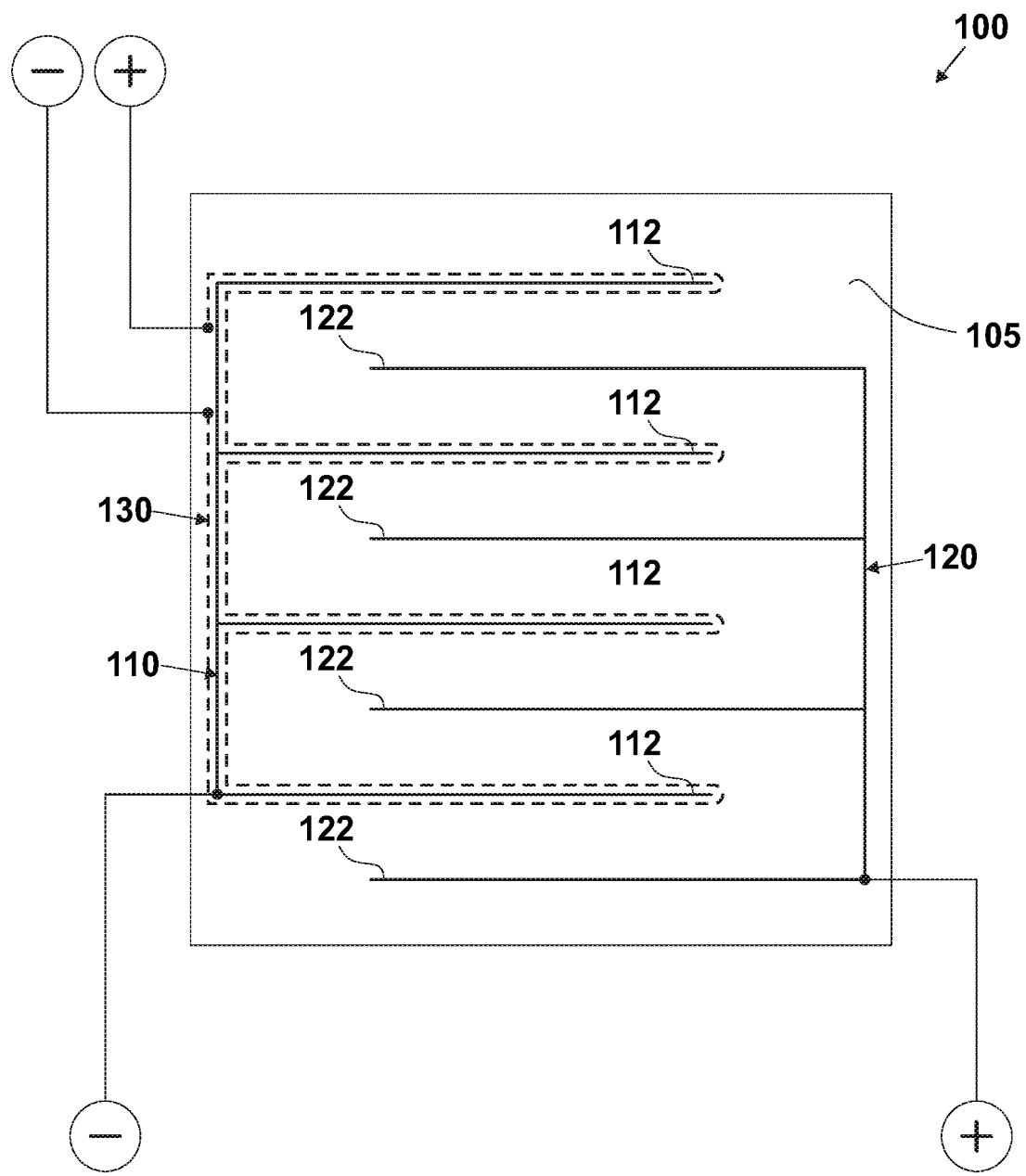
FIG. 1 diagrammatically shows a first exemplary embodiment of the textile device for detecting liquids, according to the present invention.

With reference to FIG. 1, in a possible exemplary embodiment, the textile device 100 for detecting liquids, according to the present invention, comprises a matrix fabric 105 obtained by knitting, during which a first non-insulated conductive wire 110 and a second non-insulated conductive wire 120 have been also co-knitted.

In particular, each non-insulated conductive wires 110, 120 comprises a plurality of branches 112,122 arranged in parallel mesh ranks, and knitted in alternate rows, in such a way that the non-insulated conductive wires 110,120 form respective comb structures at least partially interpenetrated and in such a way to homogeneously cover the surface of the textile device 100.

The non-insulated conductive wires 110,120 are connected to a source of electric energy, in order to create a first electric circuit and to have a potential difference between the non-insulated conductive wires 110,120. Furthermore, there is present, but not shown in the figure for simplicity, an electrical resistance measuring device configured to measure the electric resistance R in the first electric circuit.

This way, when the matrix fabric 105 is located in contact with a liquid, or with a humid or wet material, the non-insulated conductive wires 110,120 electrically connect by means of this liquid, and the electric resistance measurement device measures a variation of electric resistance R in the first electric circuit.

Furthermore, the textile device 100 comprises at least one insulated conductive wire 130 also connected to a source of electric energy to create a second electric circuit.

Advantageously, the insulated conductive wire 130 can be co-knitted with at least one of the non-insulated conductive wires 110,120, so as to simplify the manufacturing process and optimize the space on the textile device 100.

In particular, the electrical resistance measuring system is configured to measure the electric resistance R also in the second electric circuit in such a way that, since the electric resistance R is function of the temperature T, when a variation of temperature T occurs at said matrix fabric (105), the electrical resistance measuring system measures a variation of electric resistance R in the first electric circuit.

This way, the textile device 100 allows both to measure the presence of humidity and a temperature variation in the vicinity of the electrical circuits, adapting to numerous uses, such as the monitoring of these parameters on the person or inside environments.

In particular, the matrix fabric 105 can be at least partially capable of absorbing liquid. In this case, the matrix fabric can absorb the liquid or the humidity and allow the electric connection between the non-insulated conductive wires 110, 120.

In any case, both with permeable and waterproof matrix fabric, the device is also capable of detecting a liquid contained in an external damp, or wet, fabric placed in contact with the non-insulated conductive wires. Therefore, the device is capable of detecting a liquid leak even before it is moistened or wet itself.

Furthermore, the device is able both to detect the sudden presence of a liquid or a wet tissue, detecting a variation of the electrical resistance R that passes from an infinite value (open electric circuit) to a finite value (closed electric circuit), and to detect a variation in humidity, detecting a variation in the electrical resistance value R which passes between two finite values.

Furthermore, in case there are a plurality of first and second non-insulated conductive wires, the first conductive wires can be connected together with a first pole of the electrical resistance measuring device and, similarly, the second conductive wires can be connected together with a second pole of the electrical resistance measuring device.

Figure 1A:
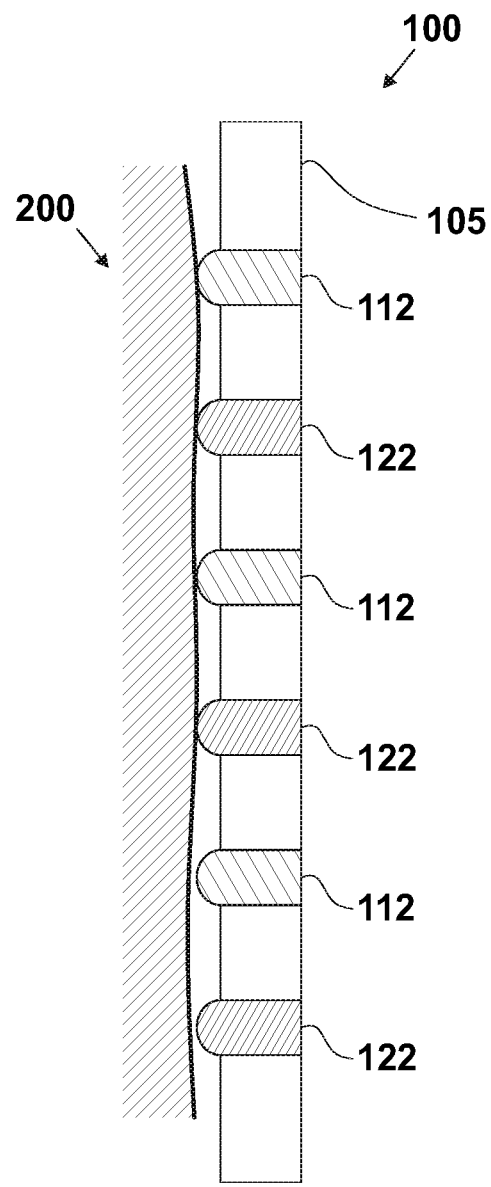
FIG. 1A shows in cross section the exemplary embodiment of the textile device for detecting liquids of FIG. 1.

With reference to FIG. 1A, in an exemplary embodiment of the invention, the non-insulated conductive wires 110,120 are knitted creating a higher thickness than the matrix fabric 105, in order to protrude with respect to it in thickness.

This embodiment makes it possible to facilitate contact between the non-insulated conductive wires 110, 120 and a surface 200 whose humidity is to be detected and which rests on the textile device 100 without sufficient pressure to fully come into contact with the matrix fabric 105. For example, this embodiment is particularly suitable to be used for clothing or linen in order to measure the conductivity of a user's skin and, in particular, his level of perspiration (Galvanic Skin Response).

Figure 2A:
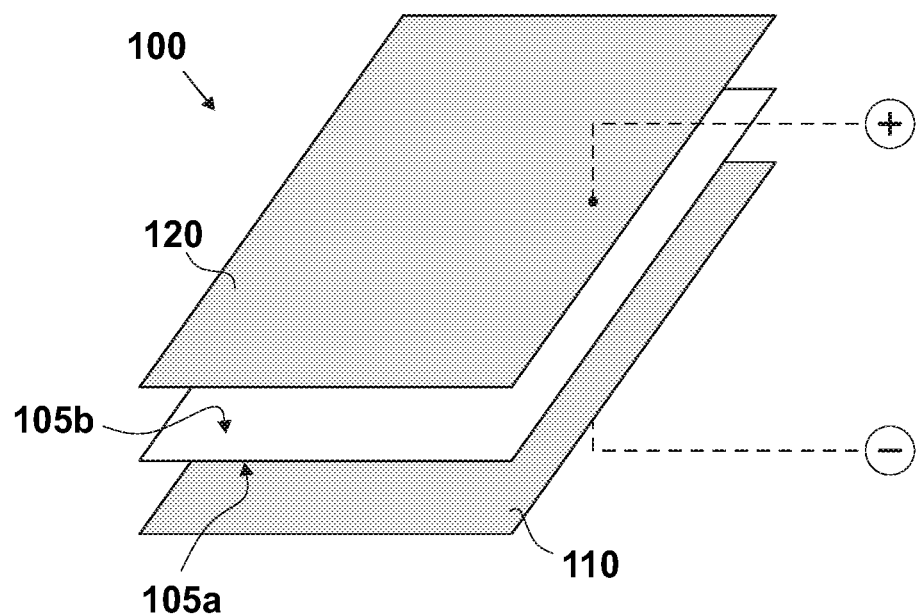
FIG. 2A diagrammatically shows a perspective view of a second exemplary embodiment of the textile device for detecting liquids, according to the present invention.
Figure 2B:
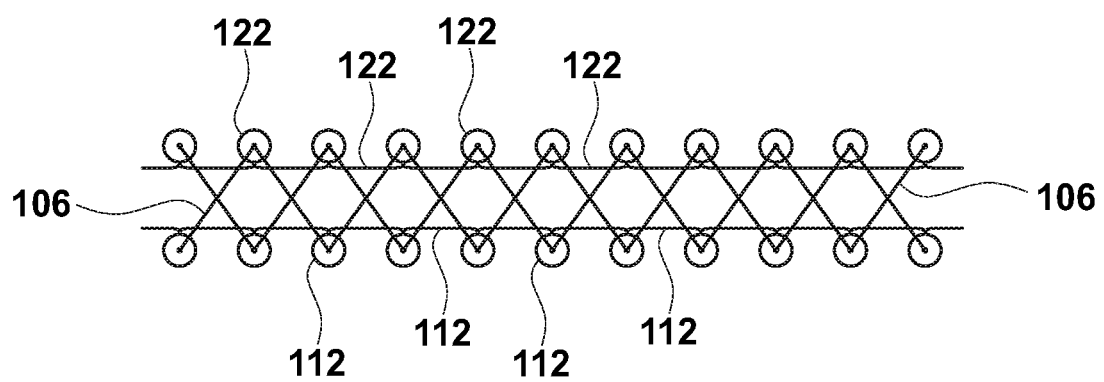
FIG. 2B diagrammatically shows in cross section the exemplary embodiment of FIG. 2A of the textile device for detecting liquids, according to the present invention.

With reference to FIGS. 2A and 2B, in an alternative exemplary embodiment of the textile device 100, the non-insulated conductive wires 110,120 are knitted with the textile wire 106 at opposite faces 105a,105b of the matrix fabric 105, in order to form a three-dimensional "sandwich" structure where the matrix fabric 105 is adapted to separate the first non-insulated conductive wire 110 and the second non-insulated conductive wire 120.

The foregoing description some exemplary specific embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realise the different functions described herein could have a different nature without, for this reason, departing from the field of the invention. it is to be understood that the phraseology or terminology that is employed herein is for the purpose of description and not of limitation.

The invention claimed is:

1. A textile device for detecting liquids comprising:
   a matrix fabric obtained by knitting;
   a first non-insulated conductive wire knitted with said matrix fabric;
   a second non-insulated conductive wire knitted with said matrix fabric;
   a source of electric energy connected to said non-insulated conductive wires in order to create a first electric circuit and to have a potential difference between said non-insulated conductive wires;
   an electrical resistance measuring system configured to measure the electric resistance R in said first electric circuit in such a way that, when said non-insulated conductive wires electrically connect by means of a liquid, said electrical resistance measuring system measures a variation of electric resistance R in said first electric circuit;
   wherein at least one insulated conductive wire is provided connected to a source of electric energy in order to create a second electric circuit;
   wherein said insulated conductive wire is co-knitted with at least one of said non-insulated conductive wires; and
   said electrical resistance measuring system is arranged to measure the electric resistance R in said second electric circuit in such a way that, since said electric resistance R is function of the temperature T, when a variation of temperature T occurs at said matrix fabric, said electrical resistance measuring system measures a variation of electric resistance R in said second electric circuit.

2. The textile device for detecting liquids, according to claim 1, wherein, when said non-insulated conductive wires electrically connect by means of said liquid, said resistance R turns from an infinite value to a finite value.

3. The textile device for detecting liquids, according to claim 1, wherein said matrix fabric is a tissue at least partially able of absorbing liquids.

4. The textile device for detecting liquids, according to claim 1, wherein each of said non-insulated conductive wires comprises a plurality of branches.

5. The textile device for detecting liquids, according to claim 4, wherein said branches of said non-insulated conductive wires are arranged in parallel mesh ranks, in such a way that said non-insulated conductive wires form respective comb structures at least partially interpenetrated.

6. The textile device for detecting liquids, according to claim 1, wherein said non-insulated conductive wires protrude from said matrix fabric, in such a way that said non-insulated conductive wires are electrically connected if located in contact with a surface containing said liquid.

\* \* \* \* \*